(12) United States Patent
Lee et al.

(10) Patent No.: US 8,958,314 B2
(45) Date of Patent: Feb. 17, 2015

(54) DATA TRANSCEIVER AND DATA-TRANSCEIVING METHOD FOR BIO-IMPLANTABLE MEDICAL DEVICES

(75) Inventors: Hoseung Lee, Gyeonggi-do (KR); Se-Ik Park, Gyeonggi-do (KR); Sung June Kim, Seoul (KR)

(73) Assignee: M. I. Tech Co., Ltd., Gyeonggi-Do (KR)

( * ) Notice: Subject to any disclaimer, the term of this patent is extended or adjusted under 35 U.S.C. 154(b) by 115 days.

(21) Appl. No.: 13/699,834

(22) PCT Filed: May 24, 2011

(86) PCT No.: PCT/KR2011/003806
§ 371 (c)(1),
(2), (4) Date: Nov. 26, 2012

(87) PCT Pub. No.: WO2011/149253
PCT Pub. Date: Dec. 1, 2011

(65) Prior Publication Data
US 2013/0070616 A1 Mar. 21, 2013

(30) Foreign Application Priority Data

May 24, 2010 (KR) .................. 10-2010-0047989
Apr. 26, 2011 (KR) .................. 10-2011-0038866

(51) Int. Cl.
| | |
|---|---|
| H04L 12/50 | (2006.01) |
| H04Q 11/00 | (2006.01) |
| H04W 56/00 | (2009.01) |
| H04L 7/10 | (2006.01) |
| A61B 5/00 | (2006.01) |
| H04L 29/08 | (2006.01) |
| H04L 1/00 | (2006.01) |

(52) U.S. Cl.
CPC ............ *H04W 56/001* (2013.01); *H04L 7/10* (2013.01); *A61B 5/0031* (2013.01); *H04L 67/12* (2013.01); *H04L 1/0061* (2013.01); *A61B 5/6846* (2013.01)
USPC ........................................... 370/250

(58) Field of Classification Search
CPC ............... H04W 56/001–56/0056; H04L 7/10
USPC ........................................ 370/350, 349
See application file for complete search history.

(56) References Cited

U.S. PATENT DOCUMENTS

| | | | |
|---|---|---|---|
| 7,688,926 B2 | 3/2010 | Suh et al. | |
| 8,442,016 B1 * | 5/2013 | Lee et al. | ............. 370/338 |

(Continued)

FOREIGN PATENT DOCUMENTS

| | | |
|---|---|---|
| JP | 2003-174382 A | 6/2003 |
| JP | 2005-286745 A | 10/2005 |

(Continued)

*Primary Examiner* — Chi H Pham
*Assistant Examiner* — Voster Preval
(74) *Attorney, Agent, or Firm* — Bacon & Thomas, PLLC (57) ABSTRACT

The invention relates a transmitter for transmitting data in bio-implantable medical devices, comprising: an activation unit which transmits, to a receiver, a predetermined number of frame bits which indicate the start of data transmission so as to activate the receiver; a preamble state notification unit which transmits, at the state where the receiver is activated or during data transmission to the receiver, a preamble data signal for turning the receiver into a preamble state; and a synchronization unit which transmits synchronization data for synchronization between the transmitter and the receiver in the preamble state.

19 Claims, 10 Drawing Sheets

(56) References Cited

U.S. PATENT DOCUMENTS

| | | |
|---|---|---|
| 2006/0031378 A1* | 2/2006 | Vallapureddy et al. ....... 709/208 |
| 2006/0200866 A1 | 9/2006 | Cameron et al. |
| 2008/0144560 A1 | 6/2008 | Jia et al. |
| 2009/0307517 A1* | 12/2009 | Fehr et al. .................. 713/500 |
| 2010/0084464 A1 | 4/2010 | Veillat |
| 2012/0119902 A1 | 5/2012 | Patro et al. |
| 2012/0170564 A1 | 7/2012 | Kim et al. |

FOREIGN PATENT DOCUMENTS

| | | |
|---|---|---|
| JP | 2006-244474 A | 9/2006 |
| JP | 2008-508081 A | 3/2008 |
| JP | 2008-242709 A | 10/2008 |
| JP | 2010-511238 A | 4/2010 |
| KR | 10-2006-0110573 B1 | 10/2006 |
| KR | 10-2009-0098890 A | 9/2009 |
| KR | 10-2010-0118960 A | 11/2010 |
| KR | 10-2011-0009405 A | 1/2011 |

* cited by examiner

DATA TRANSCEIVER AND DATA-TRANSCEIVING METHOD FOR BIO-IMPLANTABLE MEDICAL DEVICES

TECHNICAL FIELD

The present invention relates to a communication method for implantable electronic medical devices, and more particularly, to a method of performing communication in a relatively simple communication scheme in implantable medical devices, and to a transmitter and receiver using the same.

BACKGROUND ART

Implantable electronic medical devices are generally implanted into under the skin of a body, and thus, it is required to facilitate wireless communication for exchanging data with an implantable electronic medical device. Wireless communication protocols, which are presently used, are mostly for transmitting and receiving large-scale data and have a complicated hierarchical structure. Also, data that are transmitted and received based on current wireless communication protocol include voice and/or image data, and moreover include web information recently. However, it is inefficient that the complicated hierarchical structure is applied to implantable medical devices for reliably transferring small-scale data in terms of power consumption by devices or data transmission efficiency.

To date, there is no standardized communication protocol applied to implantable electronic medical devices. At present, a specific method developed by a manufacturer of an implantable electronic medical device is used.

Therefore, in implantable electronic medical devices, communication protocol is necessary for reliable communication irrespective of the kind of a channel through which data are transferred. For this reason, methods for reliable communication are being studied by those skilled in the art.

DISCLOSURE

Technical Problem

In view of the above, the present invention provides a communication method, enabling communication of implantable medical devices in a relatively simple communication scheme, for the implantable medical devices, and a transmitter and receiver using the same.

Technical Solution

In accordance with a first aspect of the present invention, there is provided a transmitter for transmitting data in an implantable medical device, the transmitter including: an activation unit configured to transmit a predetermined number of frame bits to a receiver to activate the receiver, the frame bits indicating transmission start of the data; a preamble state notification unit configured to transmit a preamble data signal for putting the receiver in a preamble state when the receiver has been activated or the data is being transmitted to the receiver; and a synchronization unit configured to transmit synchronization data for synchronization between the transmitter and the receiver in the preamble state.

In accordance with a second aspect of the present invention, there is provided a receiver for receiving transmission data supplied from a transmitter in an implantable medical device, the receiver including: a state switch unit configured to switch the receiver from a low-power state to an activation state according to a transmission initialization sequence for transmissions start and switch the activation state to the low-power state when a communication end signal for notifying transmission end of the transmission data is received; and an error check unit configured to check whether an error of the transmission data occurs through the use of an error check bit of the transmission data received from the transmitter.

In accordance with a second aspect of the present invention, there is provided a method of transmitting data from a transmitter to a receiver in an implantable medical device, the method including: transmitting channel establishment data and synchronization data to the receiver to activate and synchronize the receiver; transmitting body data to the receiver synchronized with the transmitter; transmitting a preamble data signal to switch the receiver to a preamble state in the middle of transmitting the body data; and transmitting resynchronization data for resynchronization to the receiver having the preamble state, or transmitting the body data to the receiver.

In accordance with a second aspect of the present invention, there is provided a method of receiving data transmitted from a transmitter to a receiver in an implantable medical device, the method including: switching, as channel establishment data is received from the transmitter, the receiver from a low-power mode to a start state; switching, as a preamble data signal is received, the receiver from the start state to a preamble state; receiving synchronization data in the preamble state to perform synchronization with the transmitter, and receiving body data from the transmitter; and switching, as the preamble data signal is received in the middle of receiving the body data, the receiver to the preamble state again, and receiving the resynchronization data or the body data from the transmitter.

In accordance with a second aspect of the present invention, there is provided a method of controlling a receiver using a transmitter in an implantable medical device, the method including: transmitting, by the transmitter, a control signal that enables state shift of a finite state machine of the receiver.

The control signal includes a preamble data indicator (ID) for providing a time that enables the receiver to prepare to recognize successive body data; a communication end ID for notifying transmission end of the body data; and a succession data ID for indicating succession of at least two body data.

BEST MODE

Hereinafter, embodiments of the present invention will be described in detail with reference to the accompanying drawings.

Figure 1:
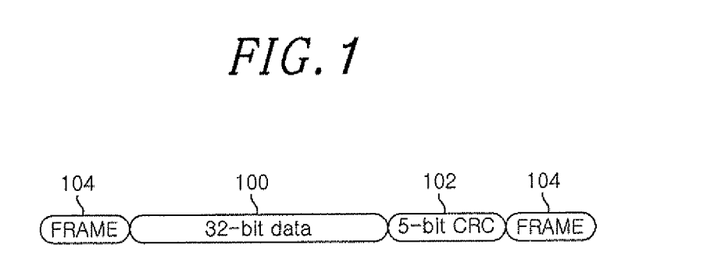
FIG. 1 is a diagram illustrating a basic structure of a data stream that defines communication protocol for communication of an implantable medical device in accordance with an embodiment of the present invention.

FIG. 1 is a diagram illustrating a basic structure of a data stream that is transmitted and received in an implantable medical device in accordance with an embodiment of the present invention.

As illustrated in FIG. 1, the data stream fundamentally includes 32-bit body data 100, a 5-bit error check code 102 for determining the transmission error of data, and a frame bit 104 for dividing the body data 100. Here, the error check code 102 is composed of a cyclic redundancy checking (CRC) code of 5 bits.

In the data stream, the frame bit 104 is used to divide the body data 100. However, a control signal for determining how for hardware (for example, components of a transmitter and receiver) to process the body data 100 is needed. According to the present invention, the control signal is defined by adding a 1-bit logic high signal (or logic low signal) after the frame bit 104, and operations of the control signal are divided with the number of logic high signals (or logic low signals). The control signal includes a preamble data indicator (ID), a communication end ID, and a succession data ID.

The preamble data ID has a function that provides a time for preparing to recognize successive data, and is defined as the combination of one frame bit and two or more 1-bit logic high signals. The communication end ID indicates the transmission end of data, and is defined as the combination of one frame bit and one 1-bit logic high signal. The succession data ID indicates the succession of two pieces of body data 100, and is defined as the combination of two frame bits.

The control signal is described with the 1-bit logic high signal as an example, but is not limited thereto. As another example, instead of the logic high signal, a logic low signal may be used.

FIGS. 2A to 2H illustrate examples of various data sequences that are transmitted and received using the control signal in the implantable medical device.

Figure 2A:
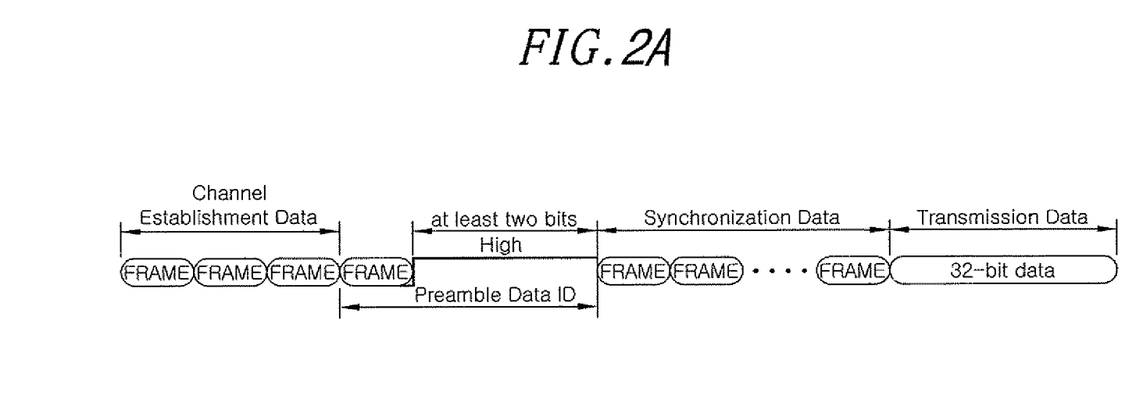
FIGS. 2A to 2H are diagrams illustrating examples of various data sequences that are transmitted and received using a control signal in the implantable medical device.

FIG. 2A illustrates a transmission initialization sequence. The transmission initialization sequence is used to establish a channel and synchronization between a transmitter and a receiver. Transmission synchronization is made with channel establishment data and synchronization data, which are divided by a preamble data ID.

The preamble data ID is composed of one frame bit and two 1-bit logic high signals. A preamble bit section of the preamble data ID has a function that provides a time enabling the receiver to prepare to recognize successive data, for example, the synchronization data. The channel establishment data is composed of at least three successive frame bits, and notifies the receiver of the transmission start of a serial data stream. When the receiver does not receive any data, the receiver automatically shifts to a low-power mode or a standby state in order to reduce operating power. However, the receiver shifts from the low-power mode to a start state that enables the reception of data succeeding the transmission initialization sequence, according to the transmission initialization sequence.

The synchronization data is composed of a plurality of frame bits. During a section of the synchronization data, the receiver accurately recognizes a rising edge of modulation data transmitted from the transmitter, and performs data synchronization for setting a reference point for demodulation of the modulation data transmitted from the transmitter. That is, by disallowing the receiver to recognize a received serial data stream as meaningful data before performing synchronization, reliable data can be received. After the receiver performs synchronization, body data may be transmitted.

Figure 2B:
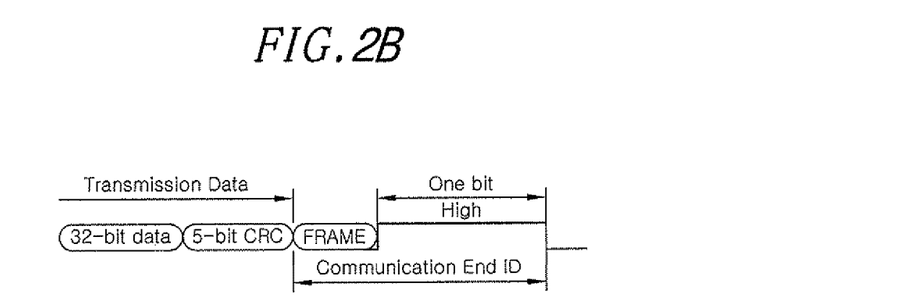

FIG. 2B illustrates a communication end sequence. The communication end sequence notifies the receiver that transmission of body data from the transmitter is completed. A communication end is made by a communication end ID succeeding the body data, and the communication end ID is composed of one frame bit and one 1-bit logic high signal.

Figure 2C:
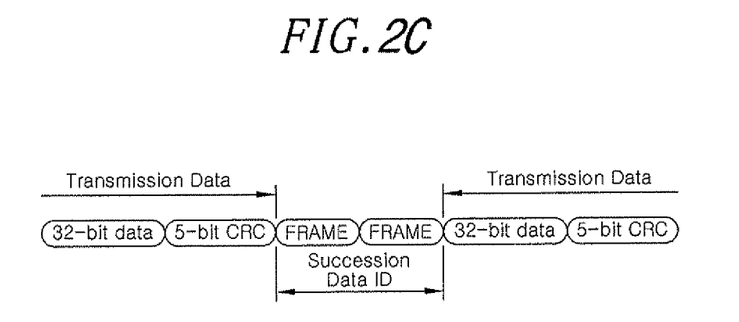

FIG. 2C illustrates a succession data transmission sequence. The succession data transmission sequence is a sequence that indicates the successive transmission of body data. The transmission of the succession data is made with one body data (including a CRC code) and a succession data ID inserted into another body data. The succession data ID includes two succession frame bits.

Figure 2D:
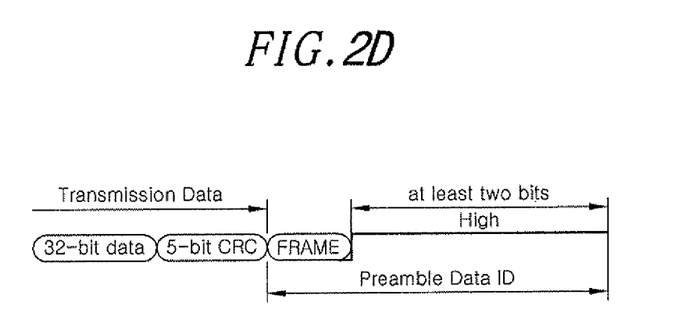

FIG. 2D illustrates a transmission standby sequence. The transmission standby sequence is a sequence that notifies the receiver that the receiver should wait for another successive sequence in the middle of transmitting body data. Transmission standby is made by a preamble data ID succeeding the body data, and the preamble data ID is composed of one frame bit and two or more 1-bit logic high signals.

Figure 2E:
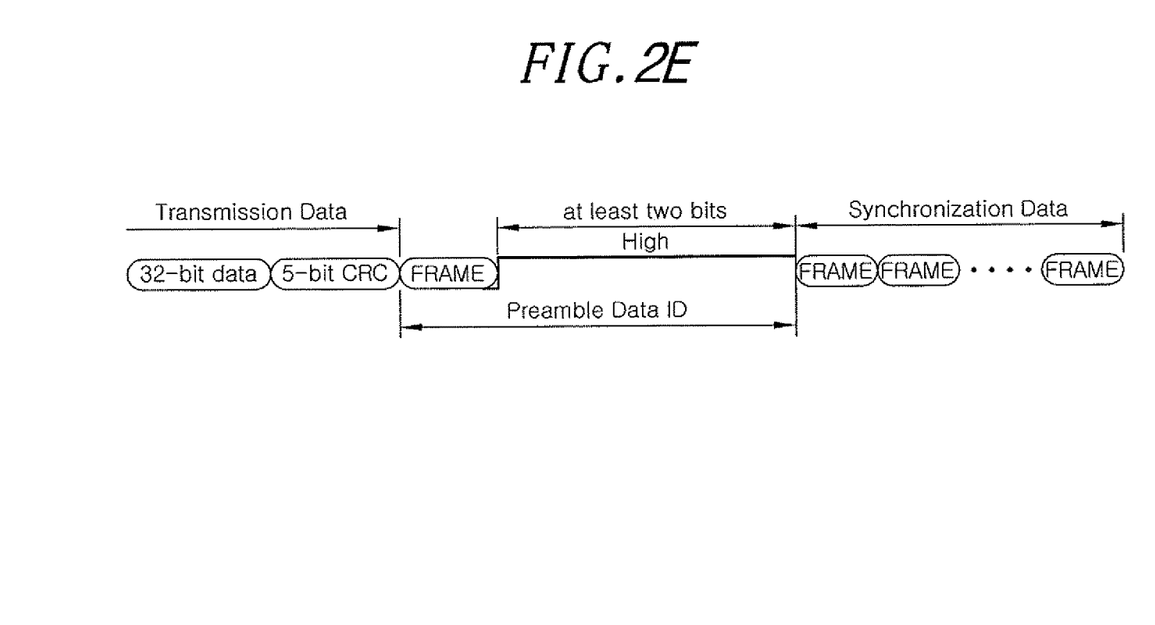

FIG. 2E illustrates a resynchronization sequence succeeding the transmission standby sequence. When data are successively transmitted for a long time, data synchronization may not be made between the transmitter and the receiver, and thus, possibility that an error of body data occurs may increase. For this reason, the receiver maintains a synchronization state (which has been made in initially establishing a channel) until the receiver recognizes the resynchronization sequence, and, after the receiver recognizes the resynchronization sequence, the receiver removes the existing synchronization and performs resynchronization. Resynchronization data is composed of a plurality of frame bits succeeding the preamble data ID of FIG. 2D.

Figure 2F:
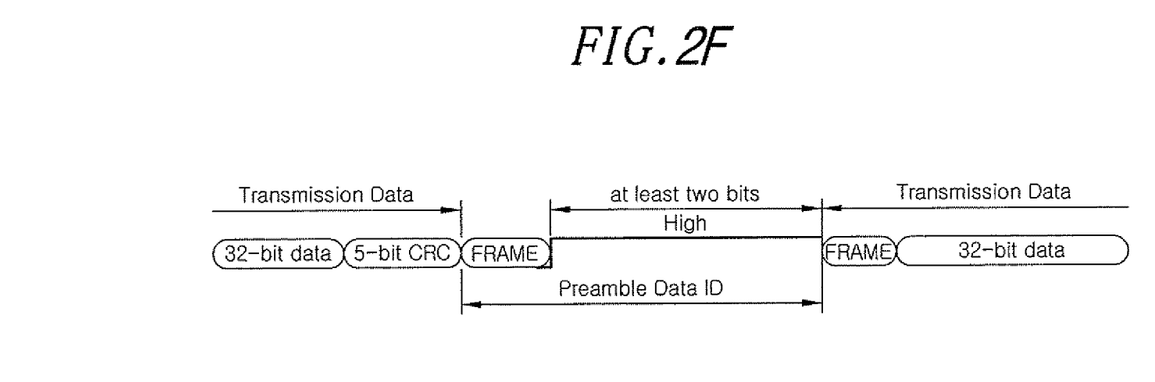

FIG. 2F illustrates transmission of body data after the transmission standby sequence. When a time for preparing data to transmit is necessary for the receiver, the transmission standby sequence may be used to allow the receiver to stand by. Body data is transmitted after the preamble data ID of FIG. 2D. In this way, by transmitting the preamble data ID to the receiver before transmitting the body data, the transmitter gains a time for preparing data to transmit and moreover puts the receiver in the standby state.

Figure 2G:
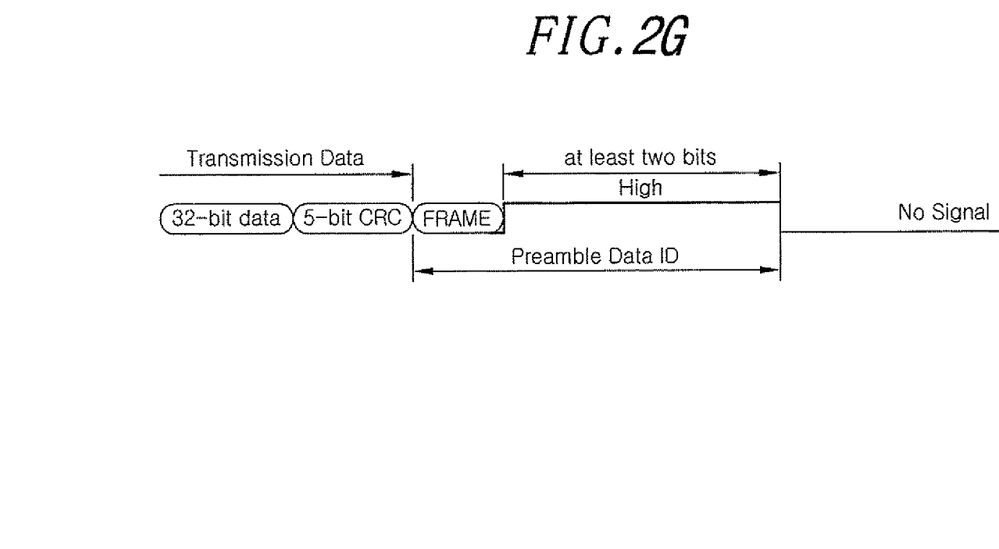
Figure 2H:
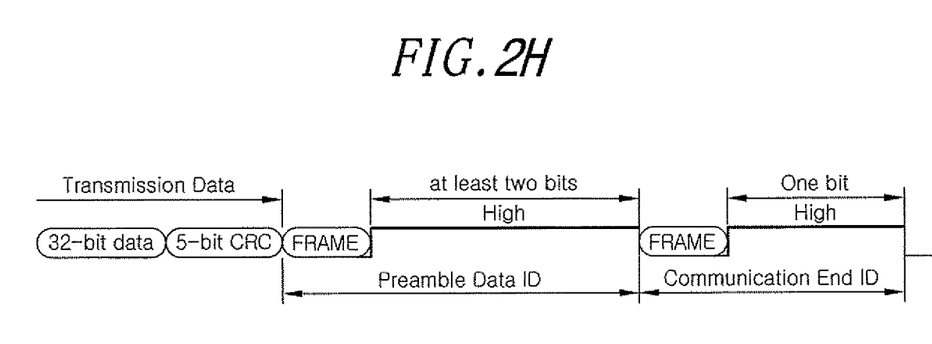

FIGS. 2G and 2H illustrate transmission end after the transmission standby sequence, respectively. The transmission end after the transmission standby sequence is used to notify the receiver of the transmission end after the transmission standby sequence. In more detail, when the transmitter requests the transmission standby of body data but the transmitter desires to end transmission for some reason, the transmission end after the transmission standby sequence notifies the receiver that the transmitter desires to end transmission. The transmission end after the transmission standby sequence, as illustrated in FIG. 2G, is made by an implicit end method that does not transmit any signal after the preamble data ID of FIG. 2D, and, as illustrated in FIG. 2H, the transmission end is made by an explicit end method that transmits the communication end ID of FIG. 2B after the preamble data ID of FIG. 2D. The receiver shifts to the low-power mode or an idle state for saving power, according to the transmission end sequence.

The above-described communication protocol in accordance with the present invention is suitable for transmitting small-scale data in implantable medical devices. As described below, when an error occurs in transmission, the receiver stores information on whether a transmission error occurs in previous transmission, and the transmitter reads the stored information to determine whether the previous transmission fails.

Figure 3:
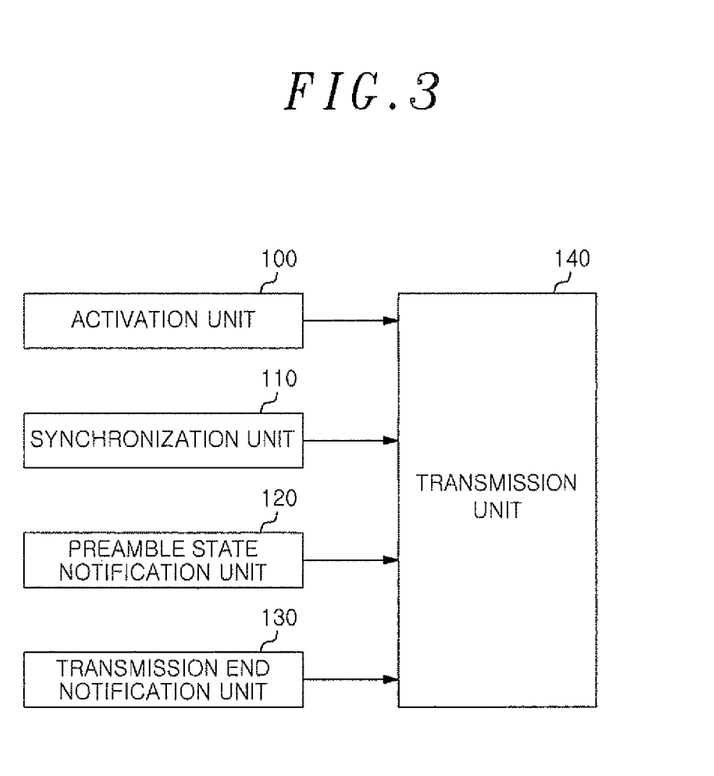
FIG. 3 illustrates a block diagram of a transmitter of the implantable medical device in accordance with an embodiment of the present invention.

FIG. 3 is a block diagram illustrating the transmitter of the implantable medical device in accordance with an embodiment of the present invention. The transmitter includes: an activation unit 100 that transmits a predetermined number of pieces of frame data for the transmission start of a data stream to activate the receiver (see FIG. 4); a synchronization unit 110 that adds and transmits synchronization data for synchronization with the receiver; a preamble state notification unit 120 that transmits a preamble data ID for notifying the receiver of a preamble state in the middle of transmitting data to the receiver for which synchronization is completed; a transmission end notification unit 130 that transmits a communication end ID for notifying the end of data transmission in the middle of transmitting data or after transmitting the preamble data; and a transmission unit 140 that encodes data supplied from the activation unit 100, the synchronization unit 110, the preamble state notification unit 120, and the transmission end notification unit 130 according to a modulation scheme and transmits the encoded data to the receiver.

When the transmitter transmits a data frame to the receiver, transmission initialization is performed, as illustrated in FIG. 2A. The activation unit 100 transmits channel establishment data composed of a plurality of frame bits to switch the receiver from the idle state or the low-power mode to the start state, for starting to communicate with the receiver. Subsequently, the synchronization unit 110 transmits synchronization data composed of a plurality of frame bits to synchronize the receiver. The channel establishment data and the synchronization data are divided by the preamble data ID.

The transmission end notification unit 130 generates the communication end ID of FIG. 2B for notifying the receiver that data transmission is ended.

As illustrated in FIG. 2A, the preamble state notification unit 120 may transmit the preamble data ID to the receiver before the receiver is activated and then synchronization with the receiver is performed. Also, as illustrated in FIG. 2C, the preamble state notification unit 120 may transmit a preamble data ID for the transmission standby of body data which is additionally supplied in the middle of transmitting body data. Also, as illustrated in FIG. 2D, the preamble state notification unit 120 may supply the preamble data ID prior to resynchronization data for resynchronization. The resynchronization data may be composed of a certain number or more of frame bits. When data are successively transmitted for a long time, data synchronization may not be made between the transmitter and the receiver, and thus, by transmitting the resynchronization data at certain intervals, data can be stably transmitted while the data are successively transmitted.

Moreover, when data are transmitted to the receiver, as illustrated in FIG. 2F, the preamble state notification unit 120 may transmit a preamble data ID before body data is transmitted. In this way, by transmitting the preamble data ID to the receiver, the transmitter gains a time for preparing data to transmit and moreover puts the receiver in the standby state.

The transmission unit 140 modulates data supplied from the activation unit 100, the synchronization unit 110, the preamble state notification unit 120, and the transmission end notification unit 130 into the data frames of FIGS. 2A to 2H, and transmits the modulated data to the receiver.

In the above description, all data streams generated by the transmitter have been described as being modulated. However, alternatively, one or more logic high (or low) signals of 1-bit configuring the control signal may be used as-is without being modulated. This is because hardware for recognizing a control signal in the receiver can be easily implemented.

Figure 4:
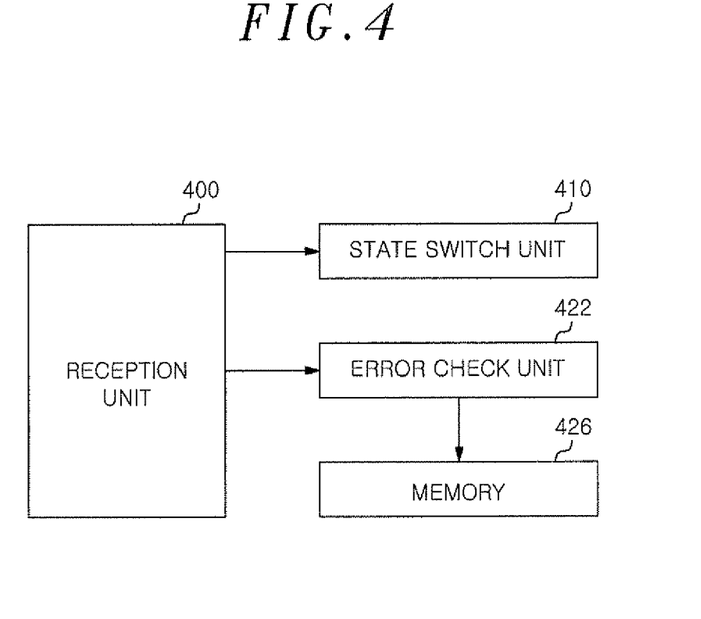
FIG. 4 illustrates a block diagram of a receiver of the implantable medical device in accordance with an embodiment of the present invention.

The receiver, which receives data from the transmitter in accordance with an embodiment of the present invention, will be described in detail with reference to FIG. 4. FIG. 4 is a block diagram illustrating the data receiver of the implantable medical device in accordance with an embodiment of the present invention.

The receiver includes a reception unit 400 that receives a modulated data stream transmitted from the transmitter, and demodulates the received data stream in a general demodulation scheme. The receiver 400 recognizes a frame bit in a demodulation operation, and recognizes an unmodulated high (or low) signal succeeding the recognized frame bit as a control signal. The receiver further includes: a state switch unit 410 that switch between states of the receiver; an error check unit 422 that checks an error of received data by using an error check code of the data received from the transmitter after the receiver is activated; and a memory 426 that stores information on whether there is an error checked by the error check unit 422.

As a certain number of frame bits included in the transmission initialization sequence of FIG. 2A are received from the transmitter, the state switch unit 410 switches the receiver from the low-power mode to the start state that is the activation state. Also, as a preamble data ID is received, the state switch unit 410 switches the receiver to the preamble state. In the preamble state, when synchronization data is received, the receiver performs synchronization with the transmitter. Also, as the communication end ID of FIG. 2B is received from the transmitter, the state switch unit 410 switches the receiver from the start state to the low-power mode.

Moreover, as illustrated in FIG. 2D, as the preamble data ID for notifying the standby state is received in the middle of receiving data, the state switch unit 410 switches the receiver to the preamble state, thereby allowing the receiver to wait for another successive sequence.

The error check unit 422 may read the information (stored in the memory 426) on whether there is an error. The transmitter may determine whether the transmission of data fails, on the basis of the error-related information, and transmit a preamble data ID and synchronization data for switching the receiver to the preamble state according to the determined result.

Figure 5:
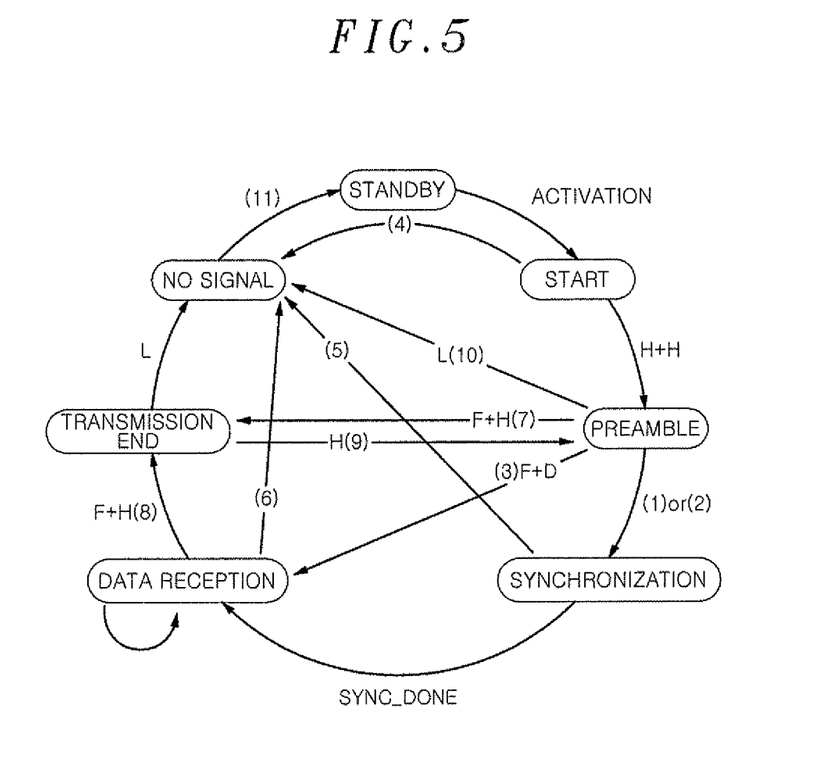
FIG. 5 is a state shift diagram illustrating an operation of the receiver of the implantable medical device in accordance with an embodiment of the present invention.

An operation, in which the operation mode of the receiver is shifted with data transmitted from the transmitter, will be described in detail with reference to FIG. 5. FIG. 5 is a state shift diagram illustrating an operation of the receiver of the implantable medical device in accordance with an embodiment of the present invention. In FIG. 5, the number in a parenthesis represents a state's turn, H and L represents logic high signal and logic low signal, respectively.

As illustrated in FIG. 5, when the receiver receives channel establishment data from the transmitter according to a transmission initialization sequence, the receiver is shifted from the low-power mode to the start state by the state switch unit 410. Also, when the receiver receives a preamble data ID from the transmitter, the receiver is switched to the preamble state by the state switch unit 410. When the receiver cannot recognize successive logic high signals in the preamble state any longer, the receiver is shifted to a state for unconditional synchronization with the transmitter (state 1).

Under a situation that the receiver has been already synchronized and is in the preamble state, as illustrated in FIG. 2E, when the receiver recognizes resynchronization data, the receiver shifts to a state for resynchronization establishment (state 2).

Under a situation that the receiver has been already established in synchronization and is in the preamble state, as illustrated in FIG. 2F, when the receiver recognizes the preamble data ID, the receiver shifts to a state in which the receiver receives data transmitted from the transmitter (state 3).

Even though the receiver has shifted to the start state with channel establishment data, when the receiver cannot recognize the preamble data ID within a certain time, the error check unit 422 sets a reception error flag, and the receiver shifts to a NO signal state (state 4).

When the receiver could not achieve synchronization in an operation of performing synchronization, the error check unit 422 sets a synchronization error flag, and the receiver shifts to the NO signal state (state 5).

While the receiver receives data, when a data stream which is not based on the communication protocol in accordance with the present invention and differs from the data stream of FIG. 1, the error check unit 422 sets a frame error flag, and the receiver shifts to the NO signal state (state 6).

In the preamble state or a data reception state, when the communication end ID of FIG. 2B is received by the receiver, the receiver shifts to a communication end state (states 7 and 8).

In the communication end state, when the preamble data ID is received by the receiver, the receiver shifts to a preamble state (state 9).

Moreover, in the preamble state, when successive low bits are received from the transmitter, the receiver shifts to the NO signal state (state 10).

When the NO signal state is continued for a predetermined time, the receiver shifts to the standby state that is the low-power mode (state 11).

The following description, as an example, will be made on a scenario in which the state of a finite state machine of the receiver shifts according to a data stream supplied from the transmitter.

Scenario 1: this corresponds to a case in which the receiver establishes an initial channel, and then receives two pieces of body data and performs an end.

In the scenario 1, a data stream is transmitted from the transmitter to the receiver in the order of FIG. 2A→FIG. 2C→FIG. 2B. Therefore, the state of the receiver shifts in the order of standby state→start state→preamble state→synchronization state→data reception state→(state shift due to a successive data transmission sequence)→data reception state→transmissions end state→NO signal state→standby state.

Scenario 2: this corresponds to a case in which the receiver further receives one piece of body data in the standby state in the scenario 1 and ends its operation.

In the scenario 2, a data stream is transmitted from the transmitter to the receiver in the order of FIG. 2A→FIG. 2C→FIG. 2F→FIG. 2B. Therefore, the state of the receiver shifts in the order of standby state→start state→preamble state→synchronization state→data reception state→(state shift due to a successive data transmission sequence)→data reception state→preamble state→transmission end state→NO signal state→standby state.

While the invention has been shown and described with respect to the embodiments, the present invention is not limited thereto. It will be understood by those skilled in the art that various changes and modifications may be made without departing from the scope of the invention as defined in the following claims.

The invention claimed is:
1. A transmitter for transmitting data in an implantable medical device, the transmitter comprising:

an activation unit configured to transmit a predetermined number of frame bits to a receiver to activate the receiver, the frame bits indicating transmission start of the data;
a preamble state notification unit configured to transmit a preamble data signal for putting the receiver in a preamble state when the receiver has been activated or the data is being transmitted to the receiver; and
a synchronization unit configured to transmit synchronization data for synchronization between the transmitter and the receiver in the preamble state,
wherein the transmitter is configured to transmit a data stream to the receiver, the data stream including body data, frame bits for dividing the body data, and a control signal,
wherein the control signal includes at least said preamble data signal,
wherein the control signal is defined by adding at least one 1-bit logic high or logic low signal after a frame bit of the data stream, and
whereby when the receiver is not yet in synchronization and receives the preamble data from the transmitter, the receiver is switched to the preamble state by a state switch unit of the receiver and, when the receiver is already in synchronization and in the preamble state, the receiver shifts to a state in which the receiver receives data transmitted from the transmitter.

2. The transmitter of claim 1, further comprising a transmission end notification unit configured to transmit a communication end signal for notifying the receiver of end of data transmission when the data is being transmitted to the receiver or the receiver is in the preamble state.

3. The transmitter of claim 2, wherein the communication end signal includes a combination of one frame bit and one logic high signal.

4. The transmitter of claim 1, wherein the synchronization unit is configured to add synchronization data to the preamble data signal at predetermined intervals and transmit it to the receiver, in order for resynchronization between the transmitter and the receiver.

5. The transmitter of claim 1, wherein the preamble data signal includes one frame bit and at least two logic high signals.

6. A receiver for receiving transmission data supplied from a transmitter in an implantable medical device, the receiver comprising:

a state switch unit configured to switch the receiver from a low-power state to an activation state according to a transmission initialization sequence for transmissions start and switch the activation state to the low-power state when a communication end signal for notifying transmission end of the transmission data is received;
an error check unit configured to check whether an error of the transmission data occurs through the use of an error check bit of the transmission data received from the transmitter; and
a preamble state notification unit configured to transmit a preamble data signal for putting the receiver in a preamble state when the receiver has been activated or the data is being transmitted to the receiver, wherein the preamble signal is defined by adding at least one 1-bit logic high or logic low signal after one of the frame bits, and
wherein when the receiver is not yet in synchronization and receives the preamble data from the transmitter, the receiver is switched to the preamble state by a state switch unit of the receiver and, when the receiver is already in synchronization and in the preamble state, the receiver shifts to a state in which the receiver receives data transmitted from the transmitter.

7. The receiver of claim 6, wherein the state switch unit is configured to perform synchronization between the receiver and the transmitter after switching the receiver to the activation state.

8. The receiver of claim 6, wherein the state switch unit is configured to switch the receiver to a preamble state when the preamble data signal is received in the middle of receiving the data from the transmitter after switching the receiver to the activation state.

9. The receiver of claim 8, wherein the state switch unit is configured to switch the receiver to the activation state when synchronization data for synchronization with the transmitter is received after switching the receiver to the preamble state.

10. The receiver of claim 8, wherein the state switch unit is configured to switch the receiver to the low-power state when a communication end signal for notifying a transmission end is received after switching the receiver to the preamble state.

11. A method of transmitting data from a transmitter to a receiver in an implantable medical device, the method comprising:
   transmitting channel establishment data and synchronization data to the receiver to activate and synchronize the receiver;
   transmitting body data and frame bits for dividing the body data to the receiver synchronized with the transmitter;
   transmitting a preamble data signal to switch the receiver to a preamble state in the middle of transmitting the body data, wherein the preamble signal is defined by adding at least one 1-bit logic high or logic low signal after one of the frame bits; and
   transmitting resynchronization data for resynchronization to the receiver having the preamble state, or transmitting the body data to the receiver,
   wherein when the receiver is not yet in synchronization and receives the preamble data from the transmitter, the receiver is switched to the preamble state by a state switch unit of the receiver and, when the receiver is already in synchronization and in the preamble state, the receiver shifts to a state for resynchronization when the resynchronization data is received from the transmitter.

12. The method of claim 11, further including transmitting a communication end signal for notifying a transmission end to the receiver of the preamble state in the middle of transmitting data or after transmitting the preamble data.

13. The method of claim 11, wherein the preamble data signal includes one frame bit and at least two logic high signals.

14. A method of receiving data transmitted from a transmitter to a receiver in an implantable medical device, the method comprising:
   switching, as channel establishment data is received from the transmitter, the receiver from a low-power mode to a start state;
   switching, as a preamble data signal is received, the receiver from the start state to a preamble state;
   receiving synchronization data in the preamble state to perform synchronization with the transmitter, and receiving body data from the transmitter; and
   switching, as the preamble data signal is received in the middle of receiving the body data, the receiver to the preamble state again, and receiving the resynchronization data or the body data from the transmitter,
   wherein the data received by the receiver includes body data, frame bits for dividing the body data, and a control signal,
   wherein the control signal includes at least said preamble data signal,
   wherein the control signal is defined by adding at least one 1-bit logic high or logic low signal after a frame bit of the data stream, and
   whereby when the receiver is not yet in synchronization and receives the preamble data from the transmitter, the receiver is switched to the preamble state by a state switch unit of the receiver and, when the receiver is already in synchronization and in the preamble state, the receiver shifts to a state in which the receiver receives data transmitted from the transmitter.

15. The method of claim 14, further comprising switching the receiver to the low-power mode when a communication end signal for notifying a transmission end is received from the transmitter in the preamble state, the start state, or the state that receives the data.

16. A method of controlling a receiver using a transmitter in an implantable medical device, the method comprising:
   transmitting, by the transmitter, a control signal that enables state shift of a finite state machine of the receiver, wherein the control signal is defined by adding at least one 1-bit logic high or logic low signal after a frame bit of the data stream,
   wherein the control signal comprises:
   a preamble data indicator (ID) for providing a time that enables the receiver to prepare to recognize successive body data;
   a communication end ID for notifying transmission end of the body data; and
   a succession data ID for indicating succession of at least two body data, and
   wherein when the receiver is not yet in synchronization and receives the preamble data indicator from the transmitter, the receiver is switched to the preamble state by a state switch unit of the receiver and, when the receiver is already in synchronization and in the preamble state, the receiver shifts to a state in which the receiver receives data transmitted from the transmitter.

17. The method of claim 16, wherein the preamble data ID includes a combination of one frame bit and at least two logic high or logic low signals of 1-bit.

18. The method of claim 16, wherein the communication end ID includes a combination of one frame bit succeeding the body data and one 1-bit logic high signal.

19. The method of claim 16, wherein the succession data ID includes a combination of two frame bits inserted between at least two pieces of successive body data.

\* \* \* \* \*